United States Patent
Swayze et al.

(10) Patent No.: US 10,918,445 B2
(45) Date of Patent: Feb. 16, 2021

(54) SURGICAL SYSTEM WITH AUGMENTED REALITY DISPLAY

(71) Applicant: Ethicon LLC, Guaynabo, PR (US)

(72) Inventors: Jeffrey S. Swayze, West Chester, OH (US); Joshua Young, Loveland, OH (US); Geoffrey S. Strobl, Williamsburg, OH (US); Andrew Beckman, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 120 days.

(21) Appl. No.: 15/383,004

(22) Filed: Dec. 19, 2016

(65) Prior Publication Data

US 2018/0168741 A1    Jun. 21, 2018

(51) Int. Cl.
*A61B 34/00* (2016.01)
*A61B 90/00* (2016.01)
(Continued)

(52) U.S. Cl.
CPC ............ *A61B 34/25* (2016.02); *A61B 5/0077* (2013.01); *A61B 5/7225* (2013.01); *A61B 17/32* (2013.01);
(Continued)

(58) Field of Classification Search
CPC ..... A61B 5/0066; A61B 3/102; A61B 3/1225; A61B 34/25; A61B 5/7225; A61B 34/20; A61B 90/37; A61B 90/36; A61B 5/0077; A61B 90/361; A61B 34/35; A61B 17/32; A61B 90/39; A61B 2090/372; A61B 34/37; A61B 5/743; A61B 90/30; A61B 2090/373; A61B 2090/3937; A61B 17/29; A61B 2090/502; A61B 2017/00061;
(Continued)

(56) References Cited

U.S. PATENT DOCUMENTS 8,114,345 B2    2/2012 Dlugos, Jr. et al.
9,492,240 B2 *  11/2016 Itkowitz ................. A61B 34/37
(Continued)

FOREIGN PATENT DOCUMENTS

WO    WO-2014151621 A1    9/2014
WO    WO-2016/133644 A1   8/2016
WO    WO-2016/149345 A1   9/2016

OTHER PUBLICATIONS

International Search Report and Written Opinion for International App. No. PCT/US2017/064588 dated Apr. 24, 2018 (17 pages).
(Continued)

*Primary Examiner* — Tung T Vo
(74) *Attorney, Agent, or Firm* — Mintz Levin Cohn Ferris Glovsky and Popeo, P.C.

(57) ABSTRACT

A surgical system includes a detector that includes an array of pixels configured to detect light reflected by a surgical device and generate a first signal. The first signal includes a first dataset representative of a visible image of the surgical device. The surgical system also includes a processor configured to receive the first signal and a second signal representative of one or more operating parameters of the surgical device. The processor is also configured to generate a modified image of the surgical device that includes information related to one or more operating parameters.

17 Claims, 10 Drawing Sheets

(51) Int. Cl.
| | |
|---|---|
| *A61B 34/35* | (2016.01) |
| *A61B 17/32* | (2006.01) |
| *G06K 9/00* | (2006.01) |
| *G06T 19/00* | (2011.01) |
| *H04N 13/239* | (2018.01) |
| *H04N 13/337* | (2018.01) |
| *H04N 13/344* | (2018.01) |
| *G06K 9/34* | (2006.01) |
| *A61B 5/00* | (2006.01) |
| *A61B 34/20* | (2016.01) |
| *G06T 11/00* | (2006.01) |
| *G06T 7/73* | (2017.01) |
| *A61B 34/37* | (2016.01) |
| *A61B 90/30* | (2016.01) |
| *A61B 17/29* | (2006.01) |
| *A61B 90/50* | (2016.01) |
| *A61B 17/00* | (2006.01) |
| *A61B 17/072* | (2006.01) |

(52) U.S. Cl.
CPC .............. *A61B 34/20* (2016.02); *A61B 34/35* (2016.02); *A61B 90/36* (2016.02); *A61B 90/361* (2016.02); *A61B 90/37* (2016.02); *A61B 90/39* (2016.02); *G06K 9/00671* (2013.01); *G06K 9/346* (2013.01); *G06T 7/73* (2017.01); *G06T 11/00* (2013.01); *G06T 19/006* (2013.01); *H04N 13/239* (2018.05); *H04N 13/337* (2018.05); *H04N 13/344* (2018.05); *A61B 5/743* (2013.01); *A61B 17/29* (2013.01); *A61B 34/37* (2016.02); *A61B 90/30* (2016.02); *A61B 2017/00017* (2013.01); *A61B 2017/00061* (2013.01); *A61B 2017/07214* (2013.01); *A61B 2034/2065* (2016.02); *A61B 2034/256* (2016.02); *A61B 2090/365* (2016.02); *A61B 2090/367* (2016.02); *A61B 2090/371* (2016.02); *A61B 2090/372* (2016.02); *A61B 2090/373* (2016.02); *A61B 2090/3937* (2016.02); *A61B 2090/3983* (2016.02); *A61B 2090/502* (2016.02); *G06K 2209/057* (2013.01); *G06T 2207/10024* (2013.01); *G06T 2207/30004* (2013.01); *G06T 2207/30204* (2013.01); *G06T 2210/41* (2013.01)

(58) Field of Classification Search
CPC ...... A61B 2034/2065; A61B 2034/256; A61B 2017/07214; A61B 2090/371; A61B 2017/00017; A61B 2090/365; A61B 2090/367; A61B 2090/3983; H04N 13/337; H04N 13/344; H04N 13/239; G06K 9/00671; G06K 2209/057; G06K 9/346; G06T 19/006; G06T 2207/30004; G06T 2207/10024; G06T 2210/41; G06T 2207/30204; G06T 11/00; G06T 7/73
USPC .......................................................... 348/77
See application file for complete search history.

(56) References Cited

U.S. PATENT DOCUMENTS

| | | | |
|---|---|---|---|
| 9,814,392 B2* | 11/2017 | Balicki | A61B 5/0066 |
| 2006/0258938 A1 | 11/2006 | Hoffman et al. | |
| 2007/0225553 A1* | 9/2007 | Shahidi | A61B 5/064 600/103 |
| 2008/0243142 A1* | 10/2008 | Gildenberg | G16H 50/50 606/130 |
| 2009/0306581 A1 | 12/2009 | Claus | |
| 2010/0168763 A1* | 7/2010 | Zhao | A61B 34/30 606/130 |
| 2010/0331855 A1* | 12/2010 | Zhao | A61B 34/30 606/130 |
| 2011/0082369 A1* | 4/2011 | Mohr | G06T 5/50 600/431 |
| 2012/0059390 A1 | 3/2012 | Mintz et al. | |
| 2012/0209288 A1* | 8/2012 | Robinson | A61B 34/30 606/130 |
| 2013/0300836 A1* | 11/2013 | Zhao | H04N 9/045 348/46 |
| 2013/0336554 A1* | 12/2013 | Lewis | G06K 9/00771 382/128 |
| 2013/0345718 A1* | 12/2013 | Crawford | A61B 17/025 606/130 |
| 2014/0055489 A1 | 2/2014 | Itkowitz et al. | |
| 2015/0031990 A1* | 1/2015 | Boctor | A61B 8/483 600/424 |
| 2015/0053742 A1* | 2/2015 | Shelton, IV | A61B 17/07207 227/175.4 |
| 2015/0145954 A1* | 5/2015 | Pulleti | B64C 39/02 348/46 |
| 2015/0170381 A1* | 6/2015 | Liu | H04N 5/23229 348/77 |
| 2015/0173644 A1* | 6/2015 | Ren | A61B 5/066 600/424 |
| 2016/0247275 A1 | 8/2016 | Chou et al. | |
| 2018/0055577 A1* | 3/2018 | Barral | A61B 34/35 |

OTHER PUBLICATIONS

European Examination Report for EP 17 818 702.7, dated Apr. 7, 2020, 7 pages.

* cited by examiner

SURGICAL SYSTEM WITH AUGMENTED REALITY DISPLAY

FIELD

Methods and devices are provided for minimally invasive surgery, and in particular for providing an augmented reality display of a surgical environment.

BACKGROUND

Minimally invasive surgical (MIS) instruments are often preferred over traditional open surgical instruments due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical environment with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical environment on a visual display at a location remote from the patient. The surgeon can typically perform the surgical procedure at the location remote from the patient whilst viewing the end effector movement on the visual display during the surgical procedure. While viewing typically a three-dimensional image of the surgical environment on the visual display, the surgeon performs the surgical procedures on the patient by manipulating master control devices at the remote location, which master control devices control motion of the remotely controlled instruments.

While significant advances have been made in the field of minimally invasive surgery, there remains a need for improved methods, systems, and devices for providing augmented reality display for a surgical environment.

SUMMARY

Methods, devices, and systems are provided for displaying an image of a surgical environment, including at least a portion of a surgical device deployed within the surgical environment, wherein the image displayed is a modified version of the surgical environment actually detected during a surgical procedure. In one embodiment the modified image displays, in addition to a portion of the surgical device, information related to one or more operating parameters the system and/or the surgical device. In another embodiment the modified image displays at least a portion of the surgical device while replacing another portion of the surgical device with an image of tissue at the surgical environment underlying the replaced portion of the surgical device.

A surgical system includes a detector that includes an array of pixels configured to detect light reflected by a surgical device and generate a first signal. The first signal includes a first dataset representative of an image of the surgical environment and the surgical device. The surgical system also includes a processor configured to receive the first signal and a second signal representative of one or more operating parameters of the surgical device. The processor is also configured to generate a modified image of the surgical device that includes at least a portion of the surgical environment and the surgical device and information related to one or more operating parameters. In one embodiment the modified image replaces one or more of at least a portion of the surgical device and at least a portion of the surgical field.

In one embodiment, the surgical system includes a display device configured to display the modified image. The display device includes at least one of a monitor and a display integrated into a head-set or other accessory (such as glasses) worn by a surgeon.

In another embodiment, the information related to the one or more parameters is displayed adjacent to the surgical device in the modified image. In yet another embodiment, the information related to the one or more parameters is displayed on the surgical device in the modified image.

In one embodiment, the first dataset comprises values representing color of the light detected by one or more pixels of the first array of pixels.

In another embodiment, the processor is configured to identify data representative of the surgical device from the first dataset to determine orientation of the surgical device based on a position of the detector with respect to the surgical device.

In one embodiment, the surgical device comprises one or more markers, each of the one or more markers configured to reflect a predetermined frequency of light. In another embodiment, the processor filters the first signal to determine orientation of the surgical device through an image recognition algorithm based on location of the one or more markers.

In one embodiment, the surgical system is a robotic surgical system and the robotic surgical system comprises at least one robotic arm configured to hold and manipulate the surgical device. In another embodiment, the surgical device has a functionality including at least one of cutting, stapling, and energy delivery.

In one embodiment, the one or more parameters includes at least one of articulation angle, shaft rotation angle, position of the knife, motion of the knife, tissue location, and reload information.

In another aspect a surgical system includes a first detector that includes a first array of pixels configured to detect light reflected by a surgical environment. The surgical environment includes a surgical site and a surgical device located at the surgical site wherein the surgical device includes one or more regions having a predetermined color. The first detector generates a first signal comprising a first dataset representative of a first image of the surgical region. The surgical system also includes a second detector that includes a second array of pixels configured to detect light reflected by the surgical environment and generate a second signal. The second signal generates a second dataset representative of a second image of the surgical environment. The surgical system also includes a processor configured to receive the first and second signals, identify, from the first and second datasets, data representative of the surgical region that does not include the one or more regions of the surgical device having the predetermined color, and generate a modified image of the surgical region based on the identified data.

In one embodiment, the predetermined color is green. In another embodiment, the first dataset includes values representing color of the light detected by one or more pixels of the first array of pixels and the second dataset includes values representing color of the light detected by one or more pixels of the second array of pixels.

In another embodiment the modified image does not include the one or more regions of the surgical device having the predetermined color. In yet another embodiment the modified image replaces a portion of an image of a surgical device within the surgical environment with a portion of an image of tissue within the surgical environment. In one aspect the image of tissue is an image of tissue underlying the replaced portion of the image of the surgical device.

In one embodiment the surgical system includes a display device configured to display the modified image.

In another aspect a surgical method comprises detecting light reflected by a surgical device; generating a first signal comprising a first dataset representative of an image of the surgical device; receiving the first signal and a second signal representative of one or more operating parameters of the surgical device; and generating a modified image of the surgical device that includes information related to one or more operating parameters.

BRIEF DESCRIPTION OF THE DRAWINGS

The invention will be more fully understood from the following detailed description taken in conjunction with the accompanying drawings, in which.

DETAILED DESCRIPTION

Figure 1:
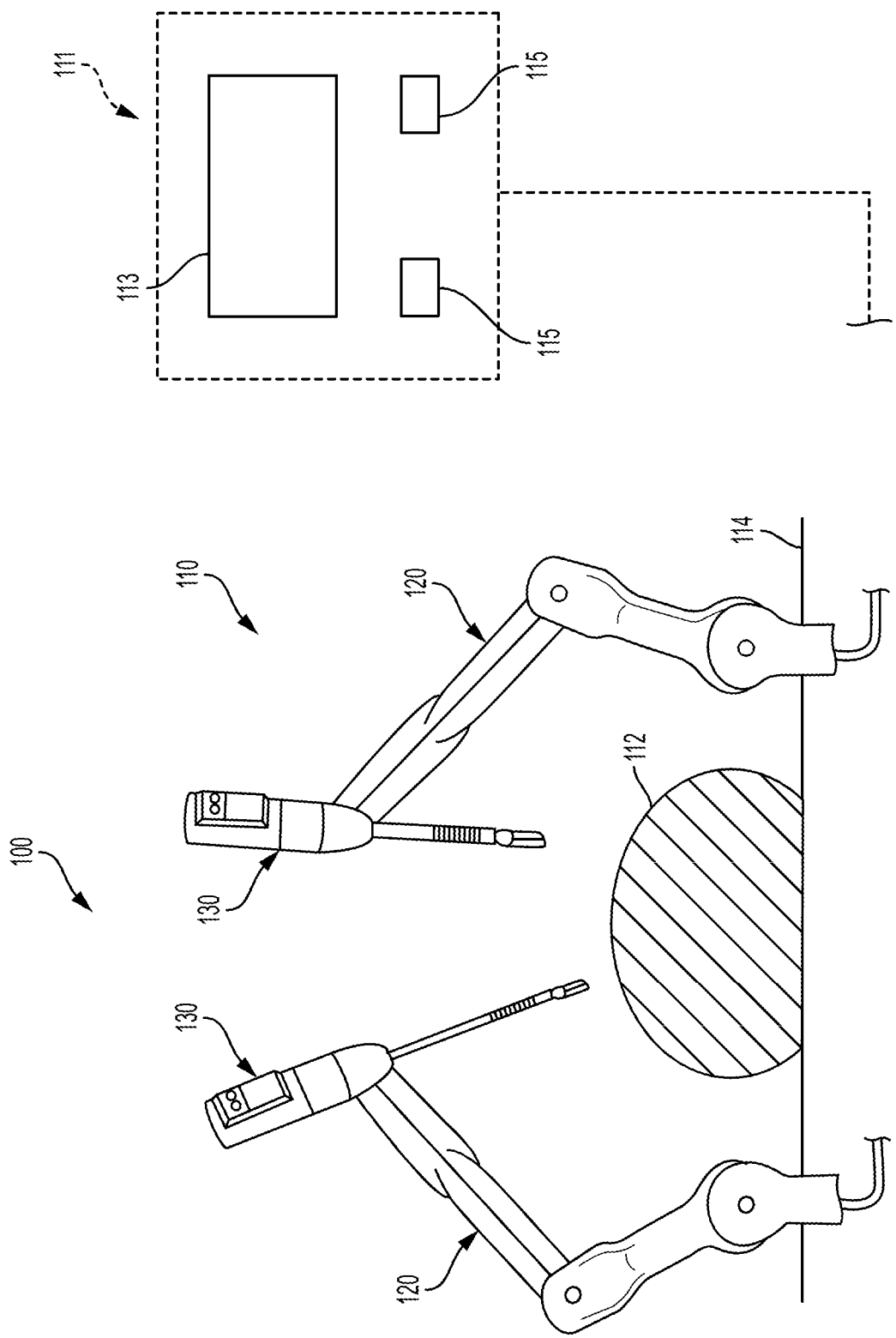
FIG. 1 illustrates a perspective view of an embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The systems, devices, and methods disclosed herein can be implemented using a robotic surgical system. WIPO Patent Publication No. WO 2014/151621 filed on Mar. 13, 2014 and entitled "Hyperdexterous Surgical System" is incorporated by reference.

In general, surgical systems are described that modify the image of a surgical environment (e.g., include surgical instruments, target tissue, and tissues surrounding the target tissue, etc.) in real-time. In particular, the image of the surgical environment can be modified to include information related to the surgery (e.g., operating parameters of the surgical instrument, patient history, surgeon checklists etc.). The image of the surgical environment can also be modified to replace the images of selected portions of the surgical instrument with those of the surgical environment (e.g., target tissues, tissues surrounding the target tissue, etc.). During a minimally invasive procedure, or any surgical procedure in which the surgical instrument is outside of the surgeon's natural field of view, an image of the surgical environment is typically generated and displayed on a display to the surgeon, such as on a video monitor, a headset, glasses, or another accessory worn by the surgeon. Such an image is typically displayed in real-time. It can be desirable to the surgeon that the image of the surgical environment is modified to include relevant surgical information. This can, for example, enable the surgeon to remain focused on the surgical field without having to look away from the image of the surgical environment during surgery. It can also be desirable to view tissues in the surgical environment whose view may be obstructed by portions of the surgical device. This can be achieved, for example, by replacing the image of the portions of the surgical device with that of tissues in the surgical environment.

In one aspect, the surgical system can track the operating parameters of the surgical instrument in real-time, and superimpose this information on the real-time image of the surgical environment. The operating parameters can be arranged in an information panel that may be located at a predetermined location in the modified image. In another aspect, the operating parameters can be distributed over the modified image. For example, operating parameters related to a part of the surgical instrument can be located at or near the related part. As the surgical instrument moves, the operating parameters can track the motion of the surgical instruments. In some embodiments, an operating parameter or a change thereof can be visually represented (e.g., change of color, flashing images etc.).

In another aspect of the surgical system, certain regions of the surgical instrument can be rendered transparent. This can be done, for example, by using chroma key technology in which the images of predetermined regions of the surgical instrument are identified and replaced with the images of target tissues that were obstructed by the surgical instrument. This can be desirable as it provides the surgeon with an unimpeded view of the target tissue during the surgical procedure.

FIG. 1 is a perspective view of one embodiment of a surgical robotic system 100 that can be used in telesurgery. The system 100 includes a patient-side portion 110 that is positioned adjacent to a patient 112, and a user-side portion 111 that is located a distance from the patient, either in the same room and/or in a remote location. The patient-side portion 110 generally includes one or more robotic arms 120 and one or more tool assemblies 130 that are configured to releasably couple to a robotic arm 120. The user-side portion 111 generally includes a vision system 113 for viewing the patient 112 and/or surgical environment, and a control system 115 for controlling the movement of the robotic arms 120 and each tool assembly 130 during a surgical procedure.

The control system 115 can have a variety of configurations and it can be located adjacent to the patient, e.g., in the operating room, remote from the patient, e.g., in a separate control room, or it can be distributed at two or more locations. As an example of a dedicated system, a dedicated system control console can be located in the operating room, and a separate console can be located at a remote location. The control system 115 can include components that enable a user to view a surgical environment of a patient 112 being operated on by the patient-side portion 110 and/or to control one or more parts of the patient-side portion 110 (e.g., to perform a surgical procedure at the surgical environment 112). In some embodiments, the control system 115 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 120 and tool assemblies 130.

The patient-side portion can also have a variety of configurations. As depicted in FIG. 1, the patient-side portion 110 can couple to an operating table 114. However, in other embodiments, the patient-side portion 110 can be mounted to a wall, to the ceiling, to the floor, or to other operating room equipment. Further, while the patient-side portion 110 is shown as including two robotic arms 120, more or fewer robotic arms 120 can be included. Furthermore, the patient-side portion 110 can include separate robotic arms 120 mounted in various positions, such as relative to the surgical table 114. Alternatively, the patient-side portion 110 can include a single assembly that includes one or more robotic arms 120 extending therefrom.

Figure 2:
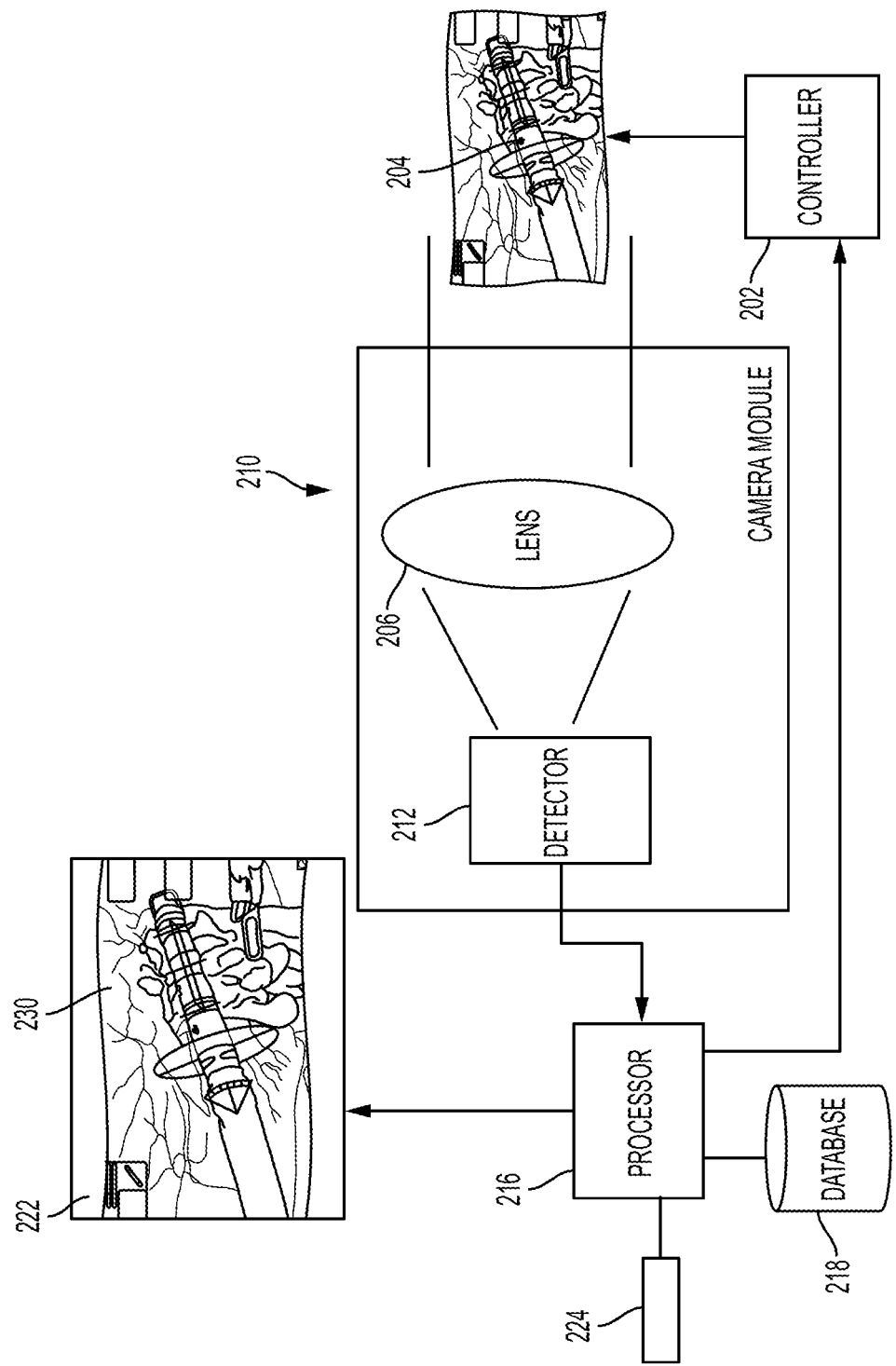
FIG. 2 illustrates a schematic view of an embodiment of a surgical system configured to generate modified images of a surgical environment.

FIG. 2 is a schematic view of an example of surgical system 200 configured to generate modified images of a surgical environment (e.g., surgical instrument 204, target tissues, tissues surrounding target tissues, etc.) in real-time to include the operating parameters of the surgical device. The surgical system 200 includes a surgical instrument 204, a controller 202 to control the operation of the surgical instrument 204, a camera module 210 configured to capture images of the surgical instrument 204, and relay one or more signals related to the captured image to a processor 216. The processor 216 can also communicate with the controller 202. For example, the processor can receive operating parameters of the surgical instrument 204 from the controller 202, and transmit control signals that can change the operating parameters to the controller 202. The processor 216 can generate a modified image that includes the image from the camera 210, and information related to the surgical procedure (e.g., operating parameters of the surgical instrument 210, checklists created by the surgeon, patient history etc.). The modified image can be displayed, on a display 222, which can be wall or table-mounted or on an accessory (e.g., a head set or glasses) worn by the surgeon. A benefit of having the image projected onto a headset or glasses is that the surgeon can simultaneously view both the projected image and the actual image. The surgical system 200 can also include an input device 224 which can communicate with the processor 216. A user (e.g., surgeon) can interact with the modified image (e.g., zoom in, zoom out, mark up, etc.) using the input device 224. Signals in the surgical system 200 (e.g., between camera module 210 and processor 216, controller 202 and processor 216, input device 224 and processor 216, etc.) can be communicated wirelessly (Bluetooth, WiFi, etc.) or through a data cable (e.g., optical fiber, coaxial cable, etc.).

A light source (not shown) can generate light which is reflected by the surgical environment. The light can be visible light (e.g., having a wavelength of about 400 nm to 800 nm) or light of a wavelength that is outside of the visible spectrum (e.g., infrared and ultraviolet light). A portion of the reflected light is captured by the camera module 210, which comprises a lens 206 configured to focus visible-light onto a detector 212. The quality of the image can be improved, for example, by placing detector 212 in the focal plane of the lens 206.

Figure 3:
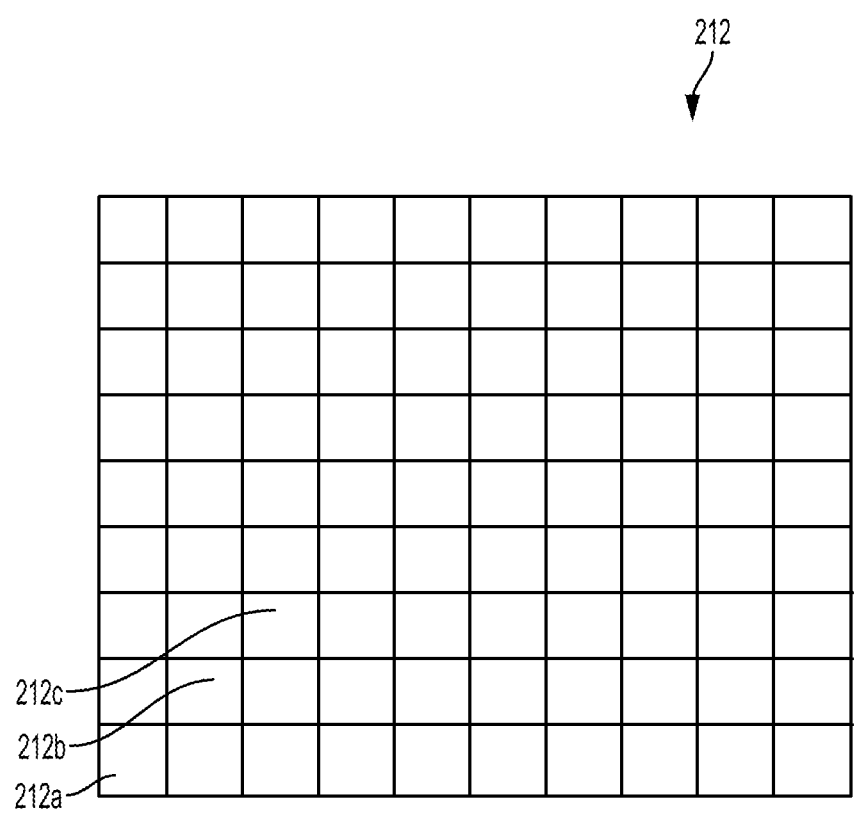
FIG. 3 illustrates a schematic view of a detector in a camera module in a surgical system.

The detector 212 is able to detect light reflected by the surgical instrument. As shown in FIG. 3, an exemplary detector 212 comprises an array of photosensitive sites (e.g., 212a-c, etc.), which can absorb electromagnetic radiation impinging on the site, and generate an electrical signal (e.g., voltage signal, current signal, etc.) that is representative of the impinged radiation. For example, the strength of the electrical signal can be proportional to the intensity of the impinged electromagnetic radiation. Photosensitive sites typically have a spectral range which determines the range of frequencies that can be efficiently detected by the site. For example, a silicon (Si) photosensitive site can detect visible to near infrared radiation (spectral range 400-1000 nm), and a germanium (Ge) or indium gallium arsenide (InGaAs) photosensitive site can detect near infrared radiation (spectral range 800-2600 nm). A suitable type of photosensitive site that is appropriate for the spectral range of the electromagnetic radiation that one wants to detect can be selected by a person skilled in the art.

A photosensitive site can be configured to detect a desired wavelength (or a narrow range of wavelength around the desired wavelength) of electromagnetic radiation that lies within its spectral range by using an optical filter. The optical filter, which is placed in the path of the electromagnetic radiation directed towards the photosensitive site, filters out all radiation except for that corresponding to the desired wavelength. For example, a Si photosensitive site (e.g., 212a) with a green color filter will primarily detect green light (approximately 500 nm).

In one example a detector (e.g., detector 212) detects an image of the surgical environment by combining the images of different regions of the object captured by various photosensitive sites in the detector. When the light reflected by the surgical instrument impinges on the detector 212, a photosensitive site therein (e.g., 212a, 212b, 212c, etc.) detects a part of the reflected light that represents an image of a region of the surgical instrument. The photosensitive site then generates an electrical signal that is representative of the captured image. This electrical signal is converted to a digital signal by an analog-to-digital converter (ADC). The digital signal has discretized values that represent, for example, the intensity of the detected radiation. As will be described below, the digital signal can also include information related to the frequency (color) of the detected radiation. The values of the digital signals from the various photosensitive sites (collectively referred to as an image dataset) are representative of the image of the surgical instrument. There can be a one-to-one relationship between a digital signal value stored in the image dataset, and the photosensitive site that has produced the digital signal value (e.g., the digital signal value can include information that identifies photosensitive site that has generated the digital signal). Therefore, by identifying a digital signal value in the image dataset the photosensitive site that generated the digital value can be identified (or vice-versa). The processor then generates the image of the surgical environment from the image dataset that can be displayed on a display device 222 (e.g., a monitor). Each pixel in the display device can represent one digital signal value in the image dataset. In other words, each pixel in the display device can represent the radiation detected by a unique photosensitive site in the detector 212.

A colored image of a surgical environment can be generated by placing optical filters (or an array of optical filters) in the path of the electromagnetic radiation directed towards a detector. For example, an array of color filters (e.g., Bayer filter, RGBE filter, CYYM filter, CYGM filter, etc.) can be placed before an array of photosensitive sites. As a result, each photosensitive site receives electromagnetic radiation of a particular wavelength (or color). For example, for a Bayer filter, each photosensitive site detects one of red, blue or green color. The processor can use a demosaicing algorithm to process an image dataset obtained using a Bayer filter to generate a "full-color" image (i.e., an image with multiple colors).

If a light optical filter is placed before the first detector 212, it will detect an image of the surgical environment. As a result, an image dataset is generated (as described above) and transmitted to the processor 216. The image dataset can include information related to the intensity and wavelength (color) of the detected light for each photosensitive site.

As described above, the controller 202 can transmit a signal to the processor 216 that includes information related to the operating parameters and identity of the surgical instrument 204. The signal may be transmitted when the controller 202 receives a request signal from the processor 216 requesting information related to the surgical instrument 204. The controller 202 can include a memory device that has a log file which tracks of the operating parameters of the surgical instrument 202. The log file (or a part thereof) can be transmitted to the processor 216. In some embodiments, the processor 216 and the controller 202 may not communicate directly. For example, their communication may be routed through one or more devices (e.g., processors, routers etc.).

The processor 216 can modify the image of the surgical environment captured by the camera module 210 by superimposing onto the captured image, information related to operating parameters. Additionally or alternately, the processor 216 can superimpose other information relevant to the surgical procedure, for example, medical history of the patient, surgeon's checklist, etc. This information can be stored in the database 218, or can be provided by a user (e.g., surgeon) through the input device 224. The modified image 230 can be displayed on the display 222.

Figure 4:
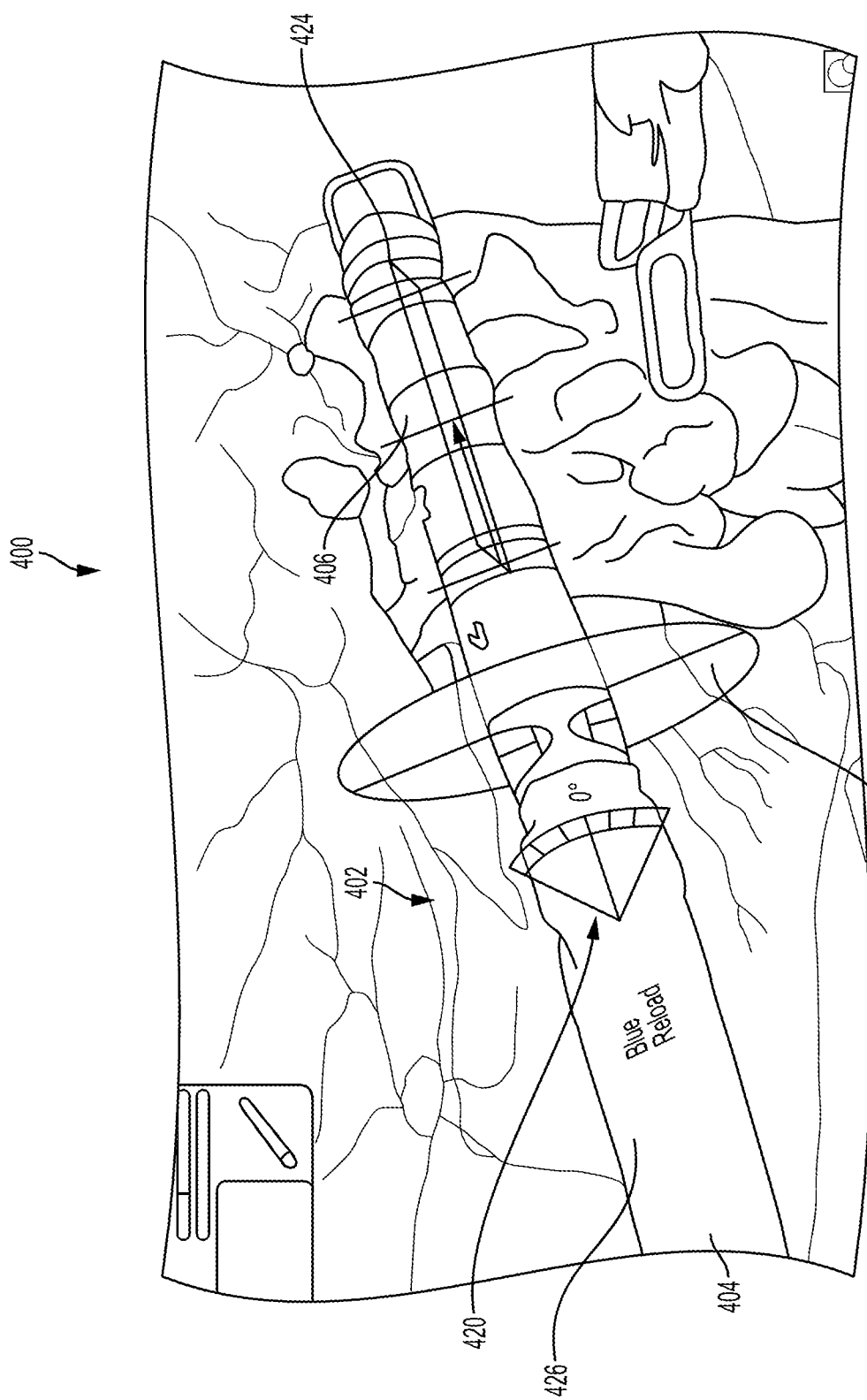
FIG. 4 illustrates an embodiment of a modified image of an surgical instrument according to a surgical system described herein.

FIG. 4 illustrates of an example of a modified image 400 of an exemplary surgical instrument 402. Various operational parameters of the surgical instrument (e.g., articulation angle 420, shaft rotation angle 422, knife location 424, reload information 426) are presented in the modified image. The operational parameters can be visually illustrated. For example, knife location 424 can be represented by an image that follows the motion of the knife in the surgical instrument in real-time. As another example, if the stapler in the surgical instrument 402 requires reloading, this information is conveyed by changing the color of the shaft 404 of the surgical instrument. The displayed operational parameters can follow the motion of the surgical instrument 402 in the modified image. In order to do so, the processor 216 identifies the image of the surgical instrument 402 from the image of the surgical environment. Additionally, the processor identifies the different parts of the surgical instrument (e.g., shaft 404, jaw 406, etc.) based on, for example, information related to the surgical instrument stored in database 218, operational parameter information from the controller 202 etc. For example, the processor can compare the identified image of the surgical instrument with an image of the surgical instrument in the database 218, and identify, using an image recognition algorithm, different parts of the surgical instrument. Once a part of the surgical instrument (e.g., shaft) is identified, an operating parameter associated with it (e.g., articulation angle) can be placed on or in proximity to its image on the display. Although the surgical instrument is illustrated to be a surgical cutting and stapling instrument, it is understood that any type of surgical instrument can be used.

The image of the surgical instrument 204 is identified by identifying the data in the image dataset that corresponds to the image of the surgical instrument captured by the camera module 210. This can be done based on a predetermined relative position between the first detector 212 and the surgical instrument 204. In this embodiment, the camera module 210 is attached to the surgical instrument 204 such that the relative position of the surgical instrument with respect to the camera module 210 remains fixed. In one example, this is accomplished by including a mounting feature on the surgical instrument to which the camera module 210 can be removably attached. Devices (detector 212, lens 206, etc.) within the camera module 210 can be positioned in a predetermined configuration. Alternatively, the devices can be attached to piezoelectric actuators that allow them to move relative to one another. This can allow the detector to detect a sharp image of the surgical instrument. For example, it can be desirable to place the detector 212 in the focal plane of the lens 206. Mechanical movements and thermal expansion of the camera module 210 and the devices therein can move the detectors out of the focal plane of the lens. The detectors can be adjusted back into the focal plane by the piezoelectric actuators that can be controlled by the processor 216, or by an input from a user. The surgical instrument 204 and the camera module 210 (and the devices within the camera module) can be adjusted to a desired predetermined position prior to the insertion of camera module 210 and surgical instrument 204 in the surgical environment. The photosensitive sites in detectors 212 that capture the image of the surgical instrument 204 can be identified based on the predetermined orientation of the detector 212 and the surgical instrument 204. Information related to the location of the aforementioned photosensitive sites can be stored in the database 218. The processor 216 can identify surgical instrument image data in the image dataset. This can be done, for example, by arranging the image data, captured by the photosensitive sites, in a predetermined pattern in the image. For example, the image data captured by the photosensitive site 212a can be placed at a predetermined location in the light dataset. Information about this relationship can be stored in an index data file in the database 218. Based on the index data file, the processor 218 can identify the image data (from the image dataset) corresponding to the image detected by the photosensitive site 212a. Alternately, the image data can include information that identifies the photosensitive site that generated it.

Figure 5:
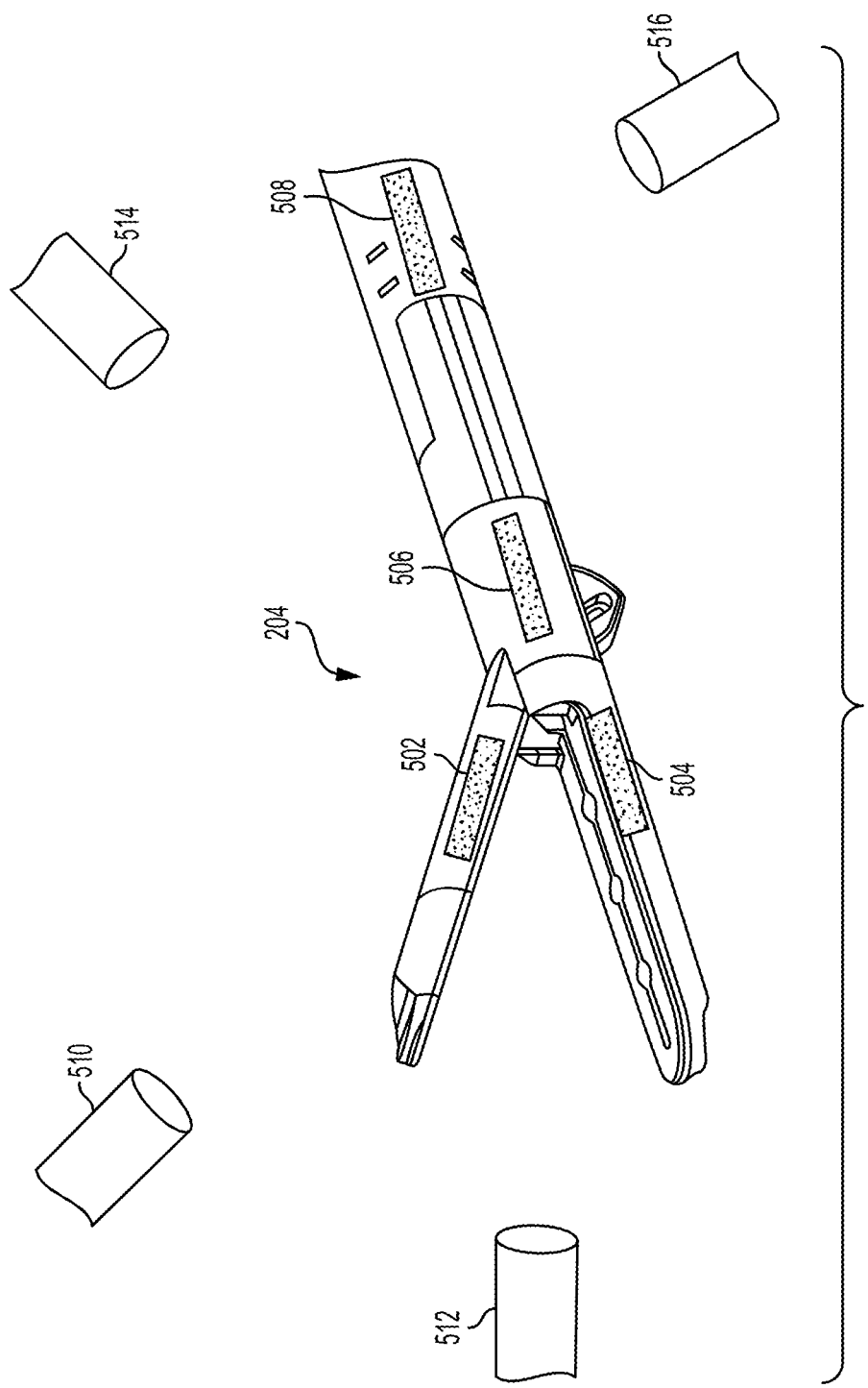
FIG. 5 illustrates a surgical instrument positioned in a field having multiple markers.

In another embodiment, the surgical instrument is identified in the image based on one or more markers on the surgical instrument 204, and multiple cameras 510, 512, 514, 516 are used to image the surgical environment. As shown in FIG. 5, the surgical instrument 204 includes a number of markers 502, 504, 506, 508 located on its surface. In one embodiment the markers are regions on the surgical instrument 204 that reflect electromagnetic radiation of a given frequency. For example, the markers can be configured to reflect light of a certain color. The color of the markers can be selected such that the color is not naturally present in the surgical environment (e.g., green, blue, etc.). The processor 216 thus identifies photosensitive sites that detect the image of the markers based on marker color. As described above, the image dataset can include, for each photosensitive site, information related to the color of the detected-light. The processor can search in the image dataset for data representative of the color of the marker. The processor 216 identifies the markers 502, 504, 506, 508 (and therefore the relative positions of the markers) in the image and compares this information with data from a database of surgical instruments stored in database 218. The database includes information related to marker color and marker position for various surgical instruments. Additionally, for a given surgical instrument, the database may include information related to the relative position of the makers in an image of the surgical instruments from multiple viewpoints. For example, the relative positions of the markers 502, 504, 506, 508 in the image of the surgical instrument 204 in the embodiment of FIG. 5 will depend on the relative position of the camera (e.g., 510, 512, 514, 516) that captures the image.

The processor can use an image recognition algorithm to identify the data in the reflected light dataset that represents the image of the surgical instrument. In one example the image recognition algorithm receives input information related to the position of the markers in the captured image, and information related to various surgical instruments stored in the database 218. The processor compares the relative positions of markers in the captured image with the orientation information of markers of the devices in the database 218 by using various pattern recognition techniques. Based on this comparison, the processor can identify data representative of image of the surgical instrument 204 in the image dataset. Additionally or alternatively, the processor can use a pattern recognition algorithm and/or device database to work with devices that are not readily known to or controlled by the robotic surgical system (i.e., a hand-operated stapler, retractors, etc.) It is to be understood that markers may comprise a specific geometric shape and/or color, either as something that is applied to the device (e.g., green dots) or the color can be inherent of typical devices (e.g., silver straight jaws and blackened shaft).

Figure 6:
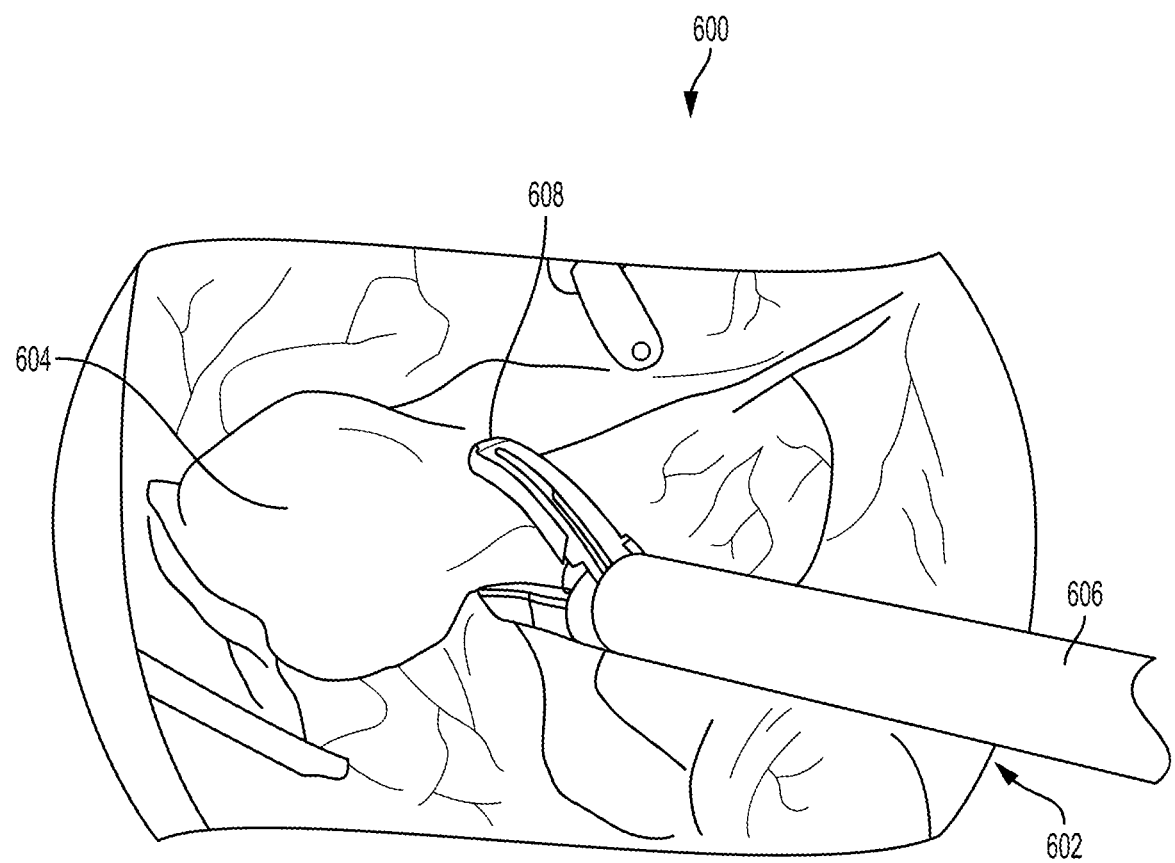
FIG. 6 illustrates an image of a surgical environment and a surgical instrument that is in use in the surgical environment.

FIG. 6 illustrates an image 600 of a surgical environment in which a surgical instrument in the form of surgical instrument 602 is in the vicinity of a target tissue 604. The surgical instrument includes a shaft 606 and an end effector 608 at the distal end of the shaft. As shown in FIG. 6, a portion of shaft 606 obstructs the view of certain portions of the target tissue that the surgeon may want to view. In the system described herein, the image 600 that is displayed to the surgeon is modified to remove the image of a portion of the shaft 606 that obstructs a view of some of the tissue and replace the shaft image with an image of the tissue that was not visible in the original image. This can be accomplished using chroma key technology where a portion of an image having a predetermined color is identified and altered (e.g., replaced with a different image). For example, the shaft 606 can be marked with a predetermined color (e.g., blue, green, etc.), which is typically one that does not naturally occur in the surgical environment. The processor 216 then identifies the image of the shaft based on its assigned color (e.g., the processor 216 can search the image dataset of the image 600 for the predetermined color). After the shaft 606 has been identified, the actual image is modified by replacing the image of the shaft with the images of one or more portions of the target tissue 604. This can be achieved by using multiple cameras (e.g., multiple camera modules 210) to capture multiple images of the surgical environment 600 from various vantage points. The processor 216 receives the multiple images, identifies the image of the shaft 606, and generates a modified image using a visual algorithm. As discussed below in more detail, the portion of the shaft that obstructs the view of tissue is replaced with a view of the underlying tissue.

Figure 7B:
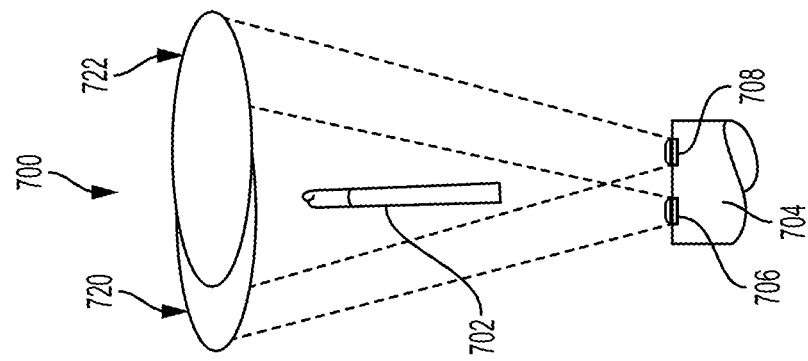
FIG. 7B illustrates another perspective view of the surgical environment of FIG. 7A.
Figure 7A:
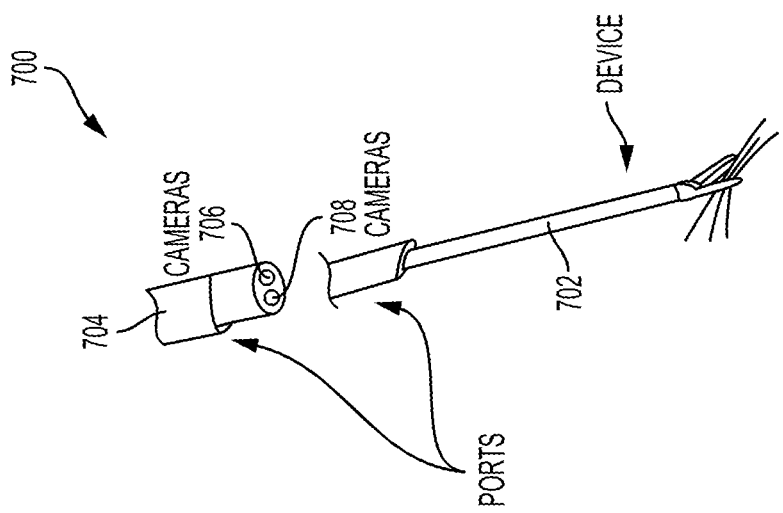
FIG. 7A illustrates a perspective view of a portion of a surgical environment.

FIG. 7A illustrates a surgical environment 700 comprising a surgical instrument 702 and a camera system 704. The camera system 704 includes two cameras 706 and 708 (e.g., camera module 210) separated by a certain distance. First camera 706 and second camera 708 capture images of the surgical instrument 702 from their respective locations and transmit the corresponding image signal to a processor (e.g., processor 216). FIG. 7B schematically illustrates a view of the surgical environment 700 from the cameras' perspective, with the field of view of the first camera 706 denoted by reference numeral 720 and the field of view of the second camera 708 denoted by reference numeral 722. The processor can use a three-dimensional (3D) image reconstruction algorithm to construct a 3D image of the entire surgical environment, or portions thereof, based on images captured by the first and second cameras 706, 708. The reconstruction algorithm takes into account the difference in perspective of the two cameras due to their separation in space.

In another embodiment, the processor can generate a stereoscopic display in which the operator's brain will combine separate 2D images to create the perception of 3D. This can be accomplished in one various ways. In one example, each 2D image is processed such that the chroma keyed device components are first removed from each 2D image. The correlated pixels of the opposing 2D image are then be stitched into this space. The two 2D images can be presented to the operator by means of a head mounted display (e.g., VR goggles) where the stitched image from the left camera is presented to the surgeon's left eye, and the right 2D image is displayed to the operator's right eye.

Alternatively, the two images can be sent to a single display and the surgeon would wear a pair of 3D glasses that allow the left eye see only the left camera image and the right eye to see only see the right image. This can be accomplished in various ways. For example, each image can be shifted slightly to only specific wavelengths and the glasses contain filters that only allow passage of light of those specific wavelengths. In another example polarization can be used to only allow the left eye to see the left camera image and the right eye to only see the right camera image. This would require each image to be polarized at an angle 90° to each other and the glasses will have corresponding polarized filters. In yet another example, the two images can also be alternated on the display and glasses worn by the surgeon can utilize shutters that are synchronized with the images displayed.

Figure 8:
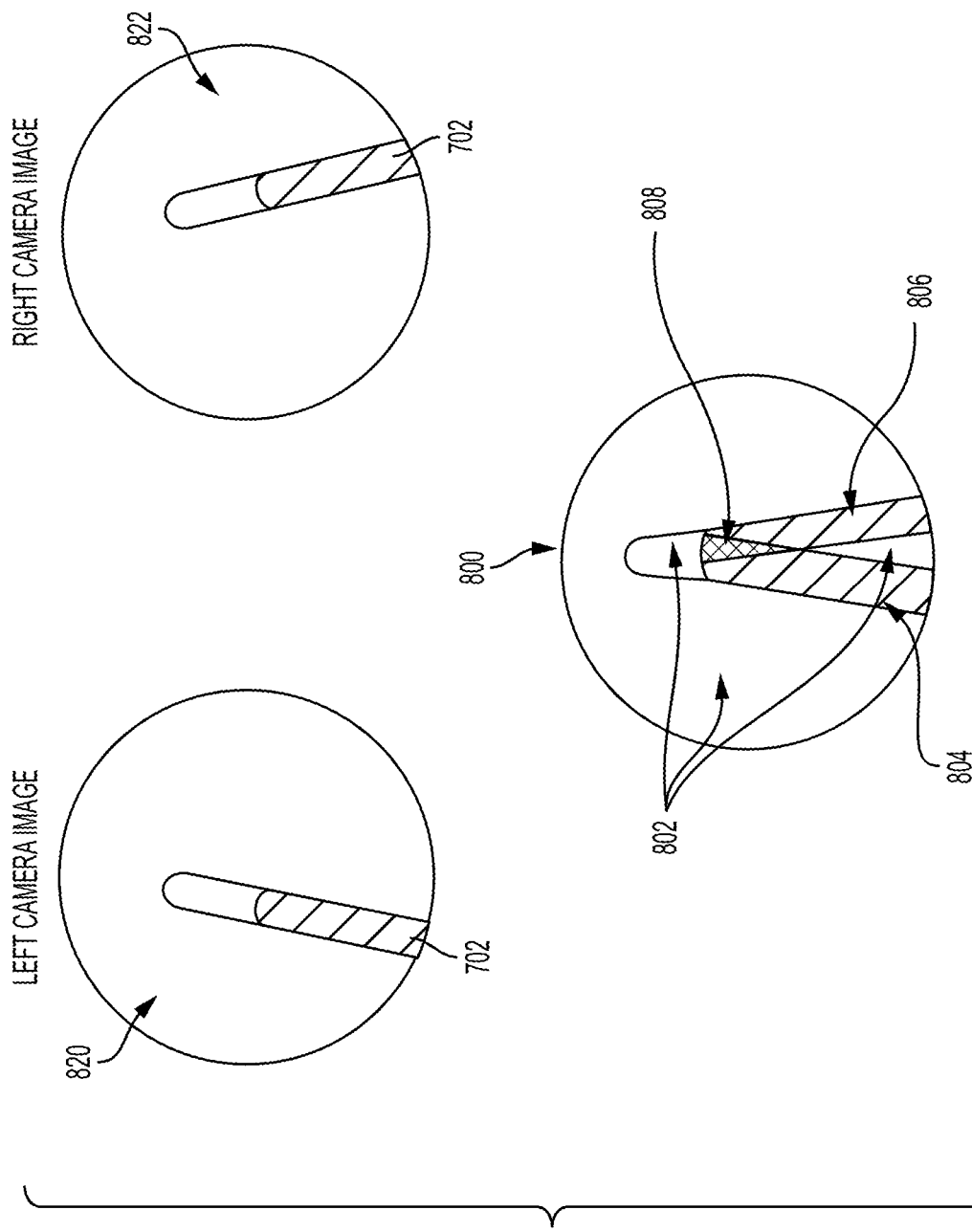
FIG. 8 schematically illustrates a combined image of a portion of the surgical environment of FIG. 7A.

FIG. 8 schematically illustrates a combined image 800 of the surgical environment 700 that is obtained by combining the first image 820 captured by the first camera 706, and the second image 822 captured by the second camera 708. Images of some portions of the surgical environment are captured by both the cameras (e.g., portion 802), while some portions are captured only by the right camera (e.g., portion 804), and other portions only by the left camera (e.g., portion 806). There are also portions of the surgical environment that may not captured by either of the two cameras, such as region 808. The processor is able to generate a 3D image for region 802 and a 2D image for regions 804 and 806. As described above, the processor can also identify predetermined regions of the surgical instrument (e.g., shaft of the surgical instrument 702). The processor can use the image reconstruction algorithm to generate a modified image of the surgical environment 700 from the combined image 800 that renders the predetermined regions of the surgical instrument (or parts thereof) transparent. In other words, in the modified image the predetermined regions of the surgical instrument are replaced by portions of the combined image, the view of which is otherwise obstructed by the predetermined regions.

Figure 9B:
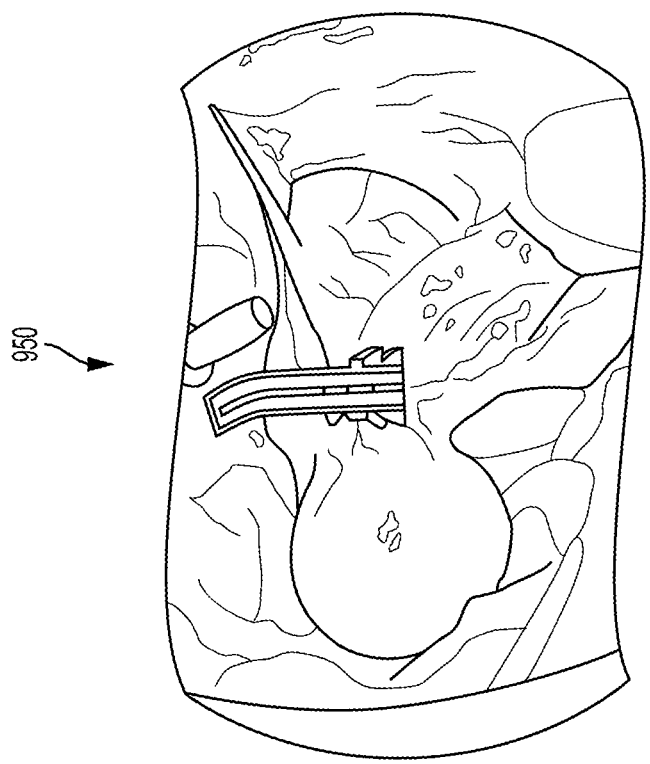
FIG. 9B illustrates a modified version of the image of FIG. 9A in which a portion of the shaft of the surgical instrument is not visible.
Figure 9A:
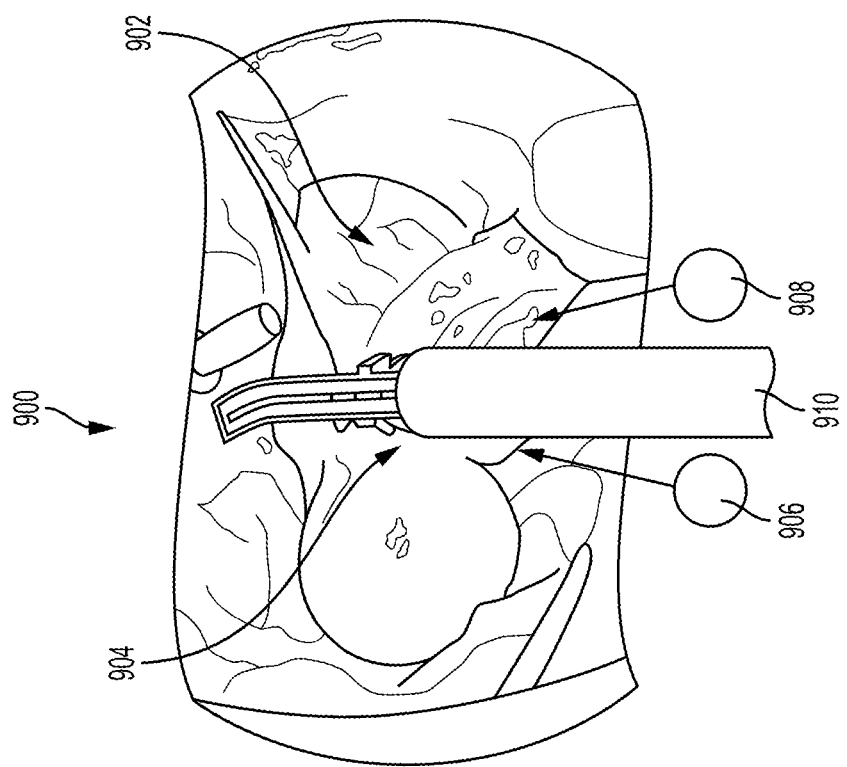
FIG. 9A illustrates an example of an image of surgical environment that includes an image of a portion of a surgical instrument.

FIG. 9A represents an example of an image of a surgical environment 900 comprising the target tissue 902 and surgical instrument 904 and a portion of shaft 910, the images of which are captured using cameras 906 and 908. FIG. 9B illustrates a modified image 950 of the surgical environment in which shaft 910 is no longer visible as it has been replaced by images of the underlying tissue.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to a user and a keyboard and a pointing device, e.g., a mouse, a trackball, etc., by which a user may provide input to the computer. Other kinds of devices can be used to provide for interaction with a user as well. For example, feedback provided to a user can be any form of sensory feedback, such as for example visual feedback, auditory feedback, or tactile feedback; and input from a user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 10:
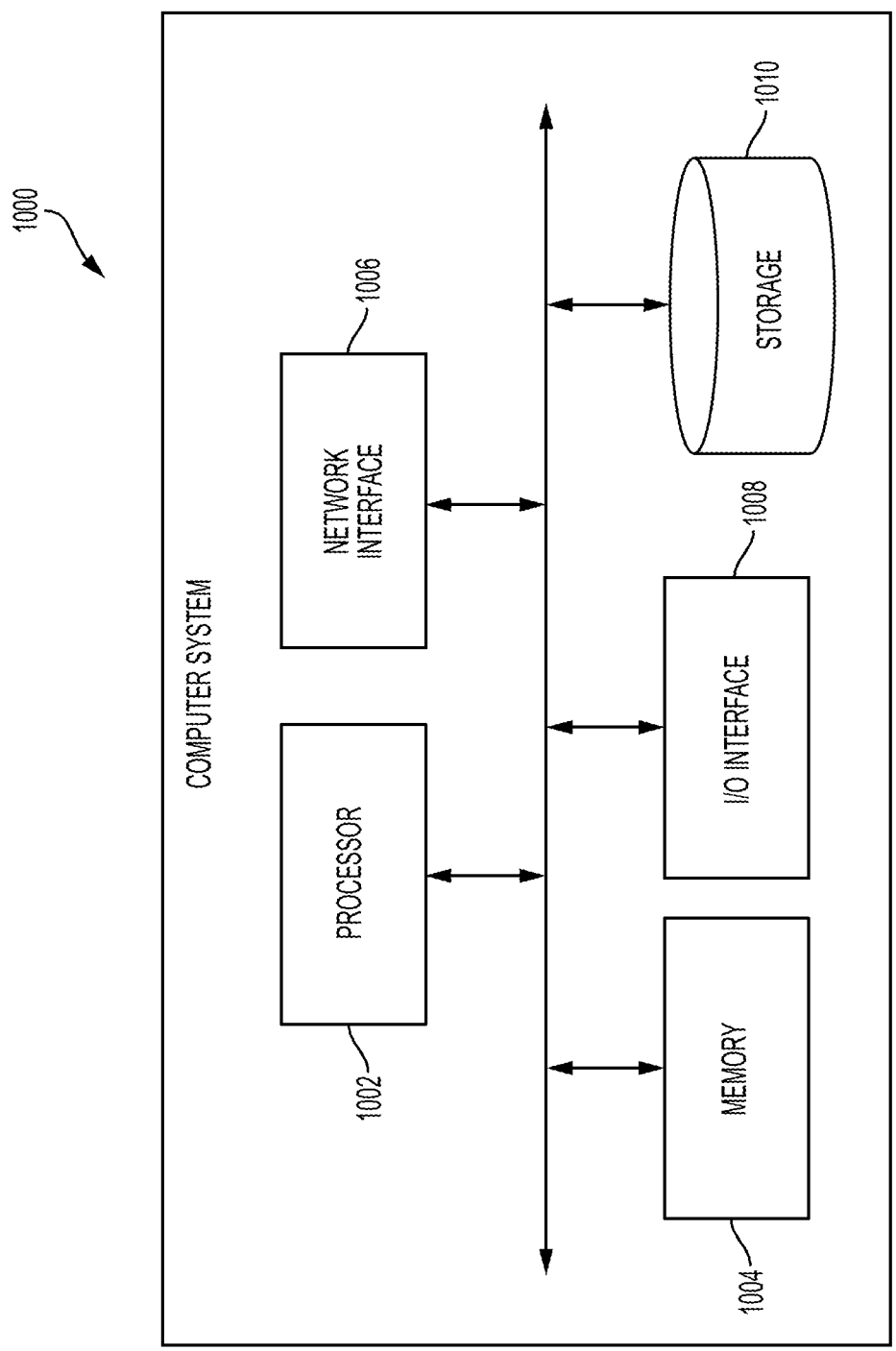
FIG. 10 is a schematic illustration of a computer system configured to generate a plurality of command signals for use with the control system described herein.

FIG. 10 illustrates an exemplary embodiment of a computer system 1000. As shown, the computer system 1000 includes one or more processors 1002 which can control the operation of the computer system 1000. "Processors" are also referred to herein as "controllers." The processor(s) 1002 can include any type of microprocessor or central processing unit (CPU), including programmable general-purpose or special-purpose microprocessors and/or any one of a variety of proprietary or commercially available single or multi-processor systems. The computer system 1000 can also include one or more memories 1004, which can provide temporary storage for code to be executed by the processor(s) 1002 or for data acquired from one or more users, storage devices, and/or databases. The memory 1004 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1000 can be coupled to a bus system 1012. The illustrated bus system 1012 is an abstraction that represents any one or more separate physical busses, communication lines/interfaces, and/or multi-drop or point-to-point connections, connected by appropriate bridges, adapters, and/or controllers. The computer system 1000 can also include one or more network interface(s) 1006, one or more input/output (TO) interface(s) 1008, and one or more storage device(s) 1010.

The network interface(s) 1006 can enable the computer system 1000 to communicate with remote devices, e.g., other computer systems, over a network, and can be, for non-limiting example, remote desktop connection interfaces, Ethernet adapters, and/or other local area network (LAN) adapters. The IO interface(s) 1008 can include one or more interface components to connect the computer system 1000 with other electronic equipment. For non-limiting example, the IO interface(s) 1008 can include high speed data ports, such as universal serial bus (USB) ports, 1394 ports, Wi-Fi, Bluetooth, etc. Additionally, the computer system 1000 can be accessible to a human user, and thus the IO interface(s) 1008 can include displays, speakers, keyboards, pointing devices, and/or various other video, audio, or alphanumeric interfaces. The storage device(s) 1010 can include any conventional medium for storing data in a non-volatile and/or non-transient manner. The storage device(s) 1010 can thus hold data and/or instructions in a persistent state, i.e., the value(s) are retained despite interruption of power to the computer system 1000. The storage device(s) 1010 can include one or more hard disk drives, flash drives, USB drives, optical drives, various media cards, diskettes, compact discs, and/or any combination thereof and can be directly connected to the computer system 1000 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 10 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 1000 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 1000 can also include a web server for generating and/or delivering the web pages to client computer systems.

In an exemplary embodiment, the computer system 1000 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system comprising:
    a detector, comprising an array of pixels configured to detect light reflected by a surgical environment that includes a surgical stapler comprising a jaw and a shaft, and generate a first signal comprising a first dataset representative of a visible image of the surgical environment and the surgical stapler; and a processor configured to:
receive the first signal and a second signal representative of one or more operating parameters of the surgical stapler,
determine an orientation of the surgical stapler,
identify the surgical stapler from the first signal based on a predetermined orientation between the detector and the surgical stapler;
identify the shaft of the surgical stapler from the first signal by comparing the identified surgical stapler with an image of the surgical stapler in a database,
determine a loading status associated with the surgical stapler;
generate a modified image in real-time that includes at least a portion of the surgical environment and the surgical stapler, and information related to the one or more operating parameters of the surgical stapler, wherein a location of the information related to the one or more operating parameters of the surgical stapler in the modified image is superimposed to be on or adjacent to an image of surgical stapler and is oriented based on the orientation of the surgical stapler,
wherein an attribute of the identified shaft is determined based on the loading status associated with the surgical stapler; and
update the location of the information related to the one or more operating parameters in the modified image based on a motion of the surgical stapler in the surgical environment in real-time.

2. The system of claim 1, further comprising a display device configured to display the modified image, wherein the display device includes at least one of a monitor and a display integrated into an accessory worn by a surgeon.

3. The system of claim 1, wherein the modified image replaces one or more of at least a portion of the surgical stapler and at least a portion of the surgical field.

4. The surgical system of claim 1, wherein the first dataset comprises values representing color of the light detected by one or more pixels of the first array of pixels.

5. The system of claim 1, wherein the processor is configured to identify data representative of the surgical instrument from the first dataset to determine orientation of the surgical instrument based on position of the detector with respect to the surgical instrument.

6. The system of claim 1, wherein the surgical stapler comprises one or more markers, each of the one or more markers configured to reflect a predetermined frequency of light.

7. The system of claim 6, wherein the processor filters the first signal to determine orientation of the surgical stapler through an image recognition algorithm based on location of the one or more markers.

8. The system of claim 1, wherein the surgical system is a robotic surgical system and the robotic surgical system comprises at least one robotic arm configured to hold and manipulate the surgical stapler.

9. The system of claim 1, wherein the surgical stapler has a functionality including at least one of cutting, stapling, and energy delivery.

10. The system of claim 1, wherein the one or more operating parameters includes at least one of articulation angle, shaft rotation angle, position of a cutting blade, motion of the cutting blade, tissue location, and reload information.

11. A surgical system comprising:
a first detector, comprising a first array of pixels configured to detect light reflected by a surgical device within a surgical environment having one or more regions with a predetermined color, the first array of pixels further being configured to generate a first signal comprising a first dataset representative of a first visible image;
a second detector, comprising a second array of pixels configured to detect light reflected by the surgical environment and generate a second signal comprising a second dataset representative of a second visible image; and
a processor configured to:
receive the first and second signals,
identify, from the first dataset, a first sub-dataset representative of the one or more regions of the surgical device having the predetermined color, and
identify, from the second dataset, a second sub-dataset representative of the one or more regions of the surgical device having the predetermined color,
generate a first modified image of the surgical environment, wherein a portion of the first visible image associated with the identified first sub-dataset is replaced with an image of underlying tissue in the surgical environment;
generate a second modified image of the surgical environment, wherein a portion of the second visible image associated with the identified second sub-dataset is replaced with an image of underlying tissue in the surgical environment; and
provide the first modified image to a first portion of a head mounted display associated with a first eye of a user, and provide the second modified image to a second portion of the head mounted display associated with a second eye of the user.

12. The surgical system of claim 11, wherein the predetermined color is green.

13. The surgical system of claim 11, wherein the first dataset comprises values representing color of the light detected by one or more pixels of the first array of pixels and the second dataset comprises values representing color of the light detected by one or more pixels of the second array of pixels.

14. The system of claim 11, further comprising a display device configured to display the modified image.

15. A surgical method comprising:
detecting light reflected by a surgical environment that includes a surgical stapler comprising a jaw and a shaft;
generating a first signal comprising a first dataset representative of an image of the surgical stapler and the surgical environment;
receiving the first signal and a second signal representative of one or more operating parameters of the surgical stapler;
determining an orientation of the surgical stapler;
identifying the surgical stapler from the first signal based on a predetermined orientation between the detector and the surgical stapler;
identifying the shaft of the surgical stapler from the first signal by comparing the identified surgical stapler with an image of the surgical stapler in a database;
determining a loading status associated with the surgical stapler;

generating a modified image in real-time that includes information related to one or more operating parameters of the surgical stapler and at least a portion of the surgical environment and the surgical stapler, wherein a location of the information related to the one or more operating parameters of the surgical stapler in the modified image is superimposed to be on or adjacent to an image of at least one of the jaw and the shaft and is oriented based on the orientation of the surgical stapler, wherein an attribute of the identified shaft is determined based on the loading status associated with the surgical stapler; and updating the location of the information related to the one or more operating parameters in the modified image based on a motion of the surgical stapler in the surgical environment in real-time.

16. The surgical system of claim 1, wherein the attribute is the color of the identified shaft in the modified image.

17. The surgical system of claim 1, wherein the detector and the surgical stapler are coupled in the predetermined orientation.

* * * * *